US011357581B2

(12) United States Patent
Mozes et al.

(10) Patent No.: US 11,357,581 B2
(45) Date of Patent: Jun. 14, 2022

(54) METHOD FOR USING A PHYSICAL OBJECT TO MANIPULATE A CORRESPONDING VIRTUAL OBJECT IN A VIRTUAL ENVIRONMENT, AND ASSOCIATED APPARATUS AND COMPUTER PROGRAM PRODUCT

(71) Applicant: NEOCIS, INC., Miami Beach, FL (US)

(72) Inventors: Alon Mozes, Miami Beach, FL (US); David Cole, Bay Harbor Islands, FL (US); Sarvagya Vaish, Miami, FL (US)

(73) Assignee: Neocis Inc., Miami, FL (US)

( * ) Notice: Subject to any disclaimer, the term of this patent is extended or adjusted under 35 U.S.C. 154(b) by 0 days.

(21) Appl. No.: 15/699,631

(22) Filed: Sep. 8, 2017

(65) Prior Publication Data

US 2018/0008355 A1    Jan. 11, 2018

Related U.S. Application Data

(63) Continuation of application No. PCT/US2016/021192, filed on Mar. 7, 2016.
(Continued)

(51) Int. Cl.
*A61C 1/00* (2006.01)
*A61C 1/08* (2006.01)
(Continued)

(52) U.S. Cl.
CPC .............. *A61B 34/25* (2016.02); *A61B 34/10* (2016.02); *A61B 34/32* (2016.02); *A61B 34/76* (2016.02);
(Continued)

(58) Field of Classification Search
CPC ......... G06T 11/00; G06T 15/00; G06T 17/00; G06T 19/00; G06T 3/20; G06T 3/60;
(Continued)

(56) References Cited

U.S. PATENT DOCUMENTS 7,716,008 B2 *    5/2010    Ohta ..................... A63F 13/10
                                              702/141
8,662,900 B2 *    3/2014    Bell, III ................ G09B 23/28
                                              434/262
(Continued)

FOREIGN PATENT DOCUMENTS

CN         104397978        3/2015
WO      WO 2013/078449      5/2013

OTHER PUBLICATIONS

McDonnell, Kevin T., Hong Qin, and Robert A. Wlodarczyk. "Virtual clay: A real-time sculpting system with haptic toolkits." Proceedings of the 2001 symposium on Interactive 3D graphics. ACM, 2001.*

(Continued)

*Primary Examiner* — Todd Buttram
(74) *Attorney, Agent, or Firm* — Womble Bond Dickinson (US) LLP

(57) ABSTRACT

Systems and methods are provided for planning a procedure. A display device is configured to display a first virtual element. A controller device having a processor is configured to be in communication with the display device, and the controller device is further configured to direct the display device to display the first virtual element. A physical control element is in communication with the controller device, and is configured to correspond to the first virtual element such that an actual manipulation of the control element is displayed, via the processor of the controller device and on the display device, as a corresponding response of the first virtual element to the actual manipulation of the control element. Associated systems, methods, and computer program products are also provided.

25 Claims, 7 Drawing Sheets

Related U.S. Application Data

Figure 1:
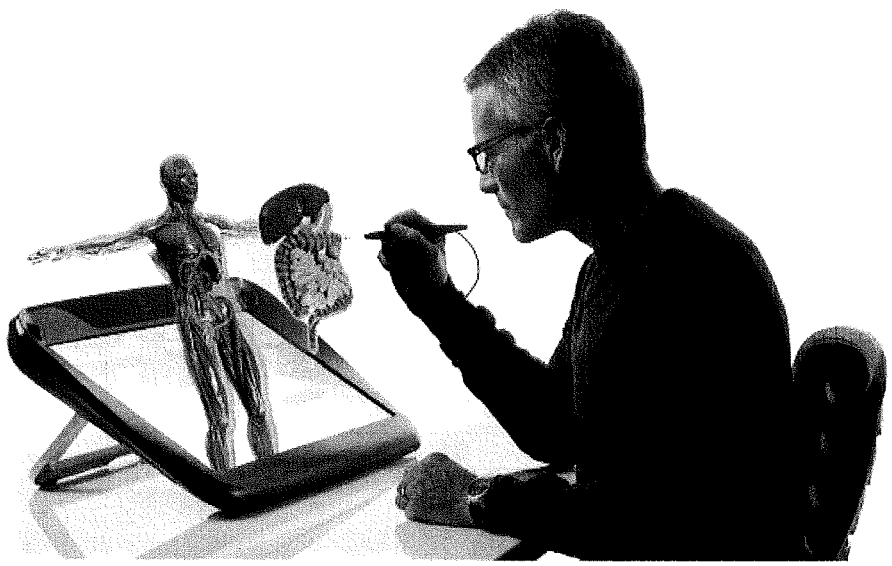

(60) Provisional application No. 62/132,105, filed on Mar. 12, 2015.

(51) Int. Cl.

| | | |
|---|---|---|
| *G06T 3/60* | (2006.01) | |
| *G06T 3/20* | (2006.01) | |
| *G06T 11/60* | (2006.01) | |
| *G06T 19/20* | (2011.01) | |
| *G06F 3/0346* | (2013.01) | |
| *A61B 34/00* | (2016.01) | |
| *A61B 34/32* | (2016.01) | |
| *G06F 3/04815* | (2022.01) | |
| *G06F 3/01* | (2006.01) | |
| *A61C 7/00* | (2006.01) | |
| *A61B 34/10* | (2016.01) | |
| *A61B 90/00* | (2016.01) | |
| *A61B 34/20* | (2016.01) | |
| *A61B 34/30* | (2016.01) | |

(52) U.S. Cl.
CPC ............ *A61C 1/0015* (2013.01); *A61C 1/084* (2013.01); *A61C 7/002* (2013.01); *G06F 3/011* (2013.01); *G06F 3/014* (2013.01); *G06F 3/04815* (2013.01); *A61B 34/30* (2016.02); *A61B 2034/101* (2016.02); *A61B 2034/102* (2016.02); *A61B 2034/105* (2016.02); *A61B 2034/107* (2016.02); *A61B 2034/2055* (2016.02); *A61B 2034/2059* (2016.02); *A61B 2034/2063* (2016.02); *A61B 2034/2068* (2016.02); *A61B 2090/363* (2016.02); *A61B 2090/364* (2016.02); *A61B 2090/3916* (2016.02); *A61B 2090/3937* (2016.02); *A61B 2090/3966* (2016.02); *A61B 2090/3991* (2016.02); *G06F 3/0346* (2013.01); *G06T 3/20* (2013.01); *G06T 3/60* (2013.01); *G06T 11/60* (2013.01); *G06T 19/20* (2013.01); *G06T 2210/41* (2013.01); *G06T 2219/2016* (2013.01)

(58) Field of Classification Search
CPC ..... G06T 11/60; G06T 19/20; G06T 2210/41; G06T 2219/2016; G06T 7/00; G06T 19/006; G06T 2215/16; G06F 17/50; G06F 17/5009; G06F 19/00; G06F 19/30; G06F 3/011; G06F 3/014; G06F 3/0346; G06F 3/04815; G06F 2111/18; G06F 3/0481; G06F 3/04817; G06F 9/4443; G06F 3/04847; G06F 11/3664; G06F 3/012; G06F 3/0304; G06F 3/11–015; A61C 1/082; A61C 1/084; A61C 3/00; A61C 8/00; A61C 8/0089; A61C 1/0015; A61C 7/002; A61B 6/14; A61B 2090/365; A61B 2090/3937; A61B 2090/3966; A61B 2090/3991; A61B 34/10; A61B 34/25; A61B 34/30; A61B 34/32; A61B 34/76; A61B 2034/101; A61B 2034/102; A61B 2034/105; A61B 2034/107; A61B 2034/2055; A61B 2034/2059; A61B 2034/2063; A61B 2034/68; A61B 2090/363; A61B 2090/364; A61B 2090/3916; G06K 9/00664–00704; H04N 5/272; H04N 2201/3245; A63F 13/10
USPC ........................................................ 345/419
See application file for complete search history.

(56) References Cited

U.S. PATENT DOCUMENTS

| | | | | |
|---|---|---|---|---|
| 2003/0097195 A1* | 5/2003 | Yamrom | ................ | G06T 19/20 700/95 |
| 2007/0279436 A1* | 12/2007 | Ng | .......................... | G06T 19/00 345/624 |
| 2008/0076566 A1* | 3/2008 | Miyamoto | .............. | A63F 13/10 463/37 |
| 2008/0278484 A1* | 11/2008 | Payandeh | ............... | G06T 17/20 345/419 |
| 2009/0263764 A1* | 10/2009 | Berckmans, III | ...... | A61C 1/084 433/215 |
| 2010/0178644 A1* | 7/2010 | Meglan | .................. | G16H 50/50 434/267 |
| 2010/0256815 A1* | 10/2010 | Salisbury | ................... | B25J 3/04 700/260 |
| 2016/0191887 A1* | 6/2016 | Casas | .................. | H04N 13/156 348/47 |
| 2016/0324598 A1* | 11/2016 | Bothorel | ................ | A61B 90/50 |

OTHER PUBLICATIONS

Debunne, Gilles, et al. "Dynamic real-time deformations using space & time adaptive sampling." Proceedings of the 28th annual conference on Computer graphics and interactive techniques. ACM, 2001.*

3shape: "Dental System ™ 2013—Implant Planning and Guided Surgery", YouTube, Mar. 12, 2013, pp. 1-1, XP054976528, Retrieved from the Internet: URL:https://www.youtube.com/watch?v=zg8gf3VtpOw—retrived on May 17, 2016, time stapm.

Anonymous: "Computer mouse—Wikipedia, the free enclyclopedia", Mar. 5, 2015, XP055272627, Retrieved from the Internet: URL:https://en.wikipedia.org/w/index.php?title=computer_mouse&olidid=650002099—Retrieved on May 15, 2016.

Anonymous: "Drag and drop—Wikipedia,the free encyclopedia", Jan. 24, 2014 (Jan. 24, 2014), XP055186807,Retrieved from the Internet:URL:http://en.wikipedia.org/w/index.php?title=Draganddrop&oldid=592127371 [retrieved on Apr. 29, 2015] the whole document.

HapTELproject: "HapTEL demo video", Aug. 24, 2009 (Aug. 24, 2009), XP054977718, Retrieved from the Internet: URL:https://www.youtube.com/watch?v-dH94oe EIa6E [retrieved on Sep. 11, 2017] 0:17-0:22 description text of video.

Kanal von voxelmansimulators: "Cavity Preparation with VOXEL-MAN Dental", YouTube, Feb. 7, 2012 XP054976530,Retrieved from the Internet:\URL:https://www.youtube.com/watch?v=CB_vdW6K42o [retrieved on May 17, 2016.].

Phattanapon: "Better Dentists through Virtual Reality", Youtube, Jan. 1, 2011 (Jan. 1, 2011), pp. 1-1, XP054976529, Retrieved from the Internet:URL:https://www.youtube.com/watch?v=XiTP9Q8JUSs [retrieved on May 17, 2016] the whole document.

Tlrptel: "Hi-tech tools for dental students",Sep. 9-13, 2010 (Sep. 13, 2016),XP054977720,Retrieved from the Internet: URL:https://www.youtube.com/watch?v=WTBJTg T Lyw E [retrieved on Sep. 11, 2017] the whole document.

\* cited by examiner

METHOD FOR USING A PHYSICAL OBJECT TO MANIPULATE A CORRESPONDING VIRTUAL OBJECT IN A VIRTUAL ENVIRONMENT, AND ASSOCIATED APPARATUS AND COMPUTER PROGRAM PRODUCT

CROSS-REFERENCE TO RELATED APPLICATIONS

This application is a continuation of International Application No. PCT/US2016/021192, filed Mar. 7, 2016, which International application was published by the International Bureau in English on Sep. 15, 2016, and which claims priority to U.S. Provisional Application No. 62/132,105, filed Mar. 12, 2015, all which are incorporated herein by reference in their entirety and for all purposes.

BACKGROUND

Field of the Disclosure

The present application relates to surgical robots and associated planning and guidance systems and, more particularly, to a planning arrangement for a guided surgical robot system used, for example, in dental surgery, wherein the planning arrangement is configured to implement a virtual object in a virtual environment, wherein the virtual object is responsive to physical manipulation of a corresponding physical object, in the same manner as the manipulated physical object, in planning and practicing the surgical procedure.

Description of Related Art

A dental implant procedure generally involves several aspects: making the diagnosis, planning the position of the implant, surgically milling the anatomy and placing the implant (i.e., an anchoring post), and then attaching the abutment and crown (i.e., prosthetic tooth/teeth). In some instance, such a procedure may be automated, for example, via a robotic surgical system. Some surgical systems, such as dental implantation surgical systems, may implement planning of the surgical procedure based on non-invasive imaging of the planned surgical site (i.e., via a CT scan). The result of the plan, namely the collected image(s) of the surgical site or patient anatomy, can thus be used, for example, for diagnosis, for surgical training, for pre-operative planning, for manufacturing a drill guide, or for guiding haptic or autonomous robotic systems.

In this regard, some such navigated and/or guided medical devices may require pre-operative planning to determine the intended course of action during surgery. Some current planning systems may, for instance, use 2D screens and interactive tools such as a mouse and keyboard in order to accomplish such a "virtual" pre-operative planning procedure. In some instances, a three-dimensional arrangement may be implemented, using, for example, a three-dimensional (3D) display arrangement, which incorporates a stereoscopic screen and 3D glasses, combined with a pen-like stylus that can be used as a pointer in the virtual space of the 3D display arrangement (see, e.g., FIG. 1). However, the manipulation of a virtual object (i.e., a dental implant or a surgical instrument) using such systems, whether by manipulating a two-dimensional (2D) object in a 2D environment, or manipulating a 3D object in a 3D environment, may not necessarily be "natural" to the user. That is, it may not necessarily be intuitive or ergonomically agreeable to manipulate the virtual object using a mouse or a stylus in a conventional manner, and various additional actions may be required by the user to impart the desired motion/movement to the virtual object (i.e., an inconvenience).

In a dental implant planning procedure using a conventional two-dimensional planning arrangement (i.e., a desktop or laptop computer), a user can, for example, generally click and drag a mouse associated with the computer to drag and drop a virtual dental implant in a desired location in a virtual space on a display screen. In some instances, the user may be required to line up circles/crosshairs with a target on each virtual object being manipulated, or the location or other object with respect to which the virtual object is being manipulated. However, such conventional manipulation of a mouse may not necessarily be effective when the planning procedure is executed by a 3D planning arrangement. Though a stylus may be used to address this issue, it remains that manipulation of the virtual object in the 3D space, using functions associated with the tip of the stylus, may not necessarily be intuitive, ergonomically agreeable, or convenient.

As such, it may be desirable to provide a planning and/or training arrangement and method, for example, for a surgical robotic system, with such a planning and/or training arrangement and method implementing a more intuitive, ergonomically agreeable, and convenient system for manipulating a virtual object, such as a dental implant or surgical instrument, in a two-dimensional or three-dimensional virtual environment, whether or not the user is significantly experienced with the system.

SUMMARY OF THE DISCLOSURE

The above and other needs are met by aspects of the present disclosure which, in one particular aspect, provides a system for planning a procedure. Such a system comprises a display device configured to display a first virtual element, and a controller device having a processor, and being configured to be in communication with the display device, so as to direct the display device to display the first virtual element. A physical control element is in communication with the controller device, and is configured to correspond to the first virtual element such that an actual manipulation of the control element is displayed, via the processor of the controller device and on the display device, as a corresponding response of the first virtual element to the actual manipulation of the control element.

Another aspect of the present disclosure provides a method for planning a procedure. Such a method comprises displaying a first virtual element on a display device with a controller device having a processor and configured to be in communication with the display device; manipulating a physical control element in communication with the controller device and configured to correspond to the first virtual element; and displaying, via the processor of the controller device and on the display device, a response of the first virtual element corresponding to the actual manipulation of the control element.

Yet another aspect provides a method for planning a procedure, comprising displaying a first virtual element via a display device; analyzing, via a processor, physical manipulation of a control element interface configured to correspond to the first virtual element; and displaying, in response to the analysis of the physical manipulation of the control element interface, a response of the first virtual element corresponding to the physical manipulation of the control element interface.

Still another aspect provides a system comprising processing circuitry operatively coupled with a control element interface, wherein the processing circuitry is configured to cause the system to at least display a first virtual element on a display device; analyze physical manipulation of a control element interface configured to correspond to the first virtual element; and display, in response to physical manipulation of the control element interface, a response of the first virtual element corresponding to the physical manipulation of the control element interface.

A further aspect provides a computer program product comprising at least one non-transitory computer readable storage medium having computer readable program instructions stored thereon. The computer readable program instructions comprise program instructions which, when executed by at least one processor implemented on a system for planning a procedure, cause the system to perform a method comprising displaying a first virtual element via a display device; analyzing, via a processor, physical manipulation of a control element interface configured to correspond to the first virtual element; and displaying, in response to the analysis of the physical manipulation of the control element interface, a response of the first virtual element corresponding to the physical manipulation of the control element interface.

The present disclosure thus includes, without limitation, the following example embodiments:

Example Embodiment 1

A system for planning a procedure, wherein such a system comprises a display device configured to display a first virtual element and a controller device having a processor. The control device is configured to be in communication with the display device, and is further configured to direct the display device to display the first virtual element. A physical control element is in communication with the controller device, wherein the control element is configured to correspond to the first virtual element such that an actual manipulation of the control element is displayed, via the processor of the controller device and on the display device, as a corresponding response of the first virtual element to the actual manipulation of the control element.

Example Embodiment 2

The system of any preceding or subsequent example embodiment, or combinations thereof, wherein the first virtual element comprises a surgical apparatus, the surgical apparatus including one of a dental implant and a surgical instrument configured to prepare a site on a jaw structure to receive the dental implant.

Example Embodiment 3

The system of any preceding or subsequent example embodiment, or combinations thereof, further comprising a selector device operably engaged with the control element, the selector device being configured to direct the controller device to one of associate and dissociate the control element with the first virtual element.

Example Embodiment 4

The system of any preceding or subsequent example embodiment, or combinations thereof, further comprising a second virtual element selectively displayed by the display device, the second virtual element being configured to interact with the first virtual element.

Example Embodiment 5

The system of any preceding or subsequent example embodiment, or combinations thereof, wherein the second virtual element includes a representation of a jaw structure.

Example Embodiment 6

The system of any preceding or subsequent example embodiment, or combinations thereof, wherein the actual manipulation of the control element includes one of translational motion and rotational motion, and the corresponding response of the first virtual element displayed on the display device includes the one of translational motion and rotational motion.

Example Embodiment 7

The system of any preceding or subsequent example embodiment, or combinations thereof, wherein the display device is configured to display the first virtual element as one of a two-dimensional image and a three-dimensional image.

Example Embodiment 8

A method for planning a procedure, wherein such a method comprises displaying a first virtual element on a display device with a controller device having a processor and configured to be in communication with the display device; manipulating a physical control element, the control element being in communication with the controller device and being configured to correspond to the first virtual element; and displaying, via the processor of the controller device and on the display device, a response of the first virtual element corresponding to the actual manipulation of the control element.

Example Embodiment 9

The method of any preceding or subsequent example embodiment, or combinations thereof, wherein displaying a first virtual element further comprises displaying a first virtual element comprising a surgical apparatus, the surgical apparatus including one of a dental implant and a surgical instrument configured to prepare a site on a jaw structure to receive the dental implant.

Example Embodiment 10

The method of any preceding or subsequent example embodiment, or combinations thereof, further comprising directing the controller device to one of associate and dissociate the control element with the first virtual element, with a selector device operably engaged with the control element.

Example Embodiment 11

The method of any preceding or subsequent example embodiment, or combinations thereof, further comprising selectively displaying a second virtual element on the display device, the second virtual element being configured to interact with the first virtual element.

Example Embodiment 12

The method of any preceding or subsequent example embodiment, or combinations thereof, wherein selectively displaying a second virtual element further comprises selectively displaying a second virtual element including a representation of a jaw structure.

Example Embodiment 13

The method of any preceding or subsequent example embodiment, or combinations thereof, wherein manipulating the control element further comprises manipulating the control element to impart one of translational motion and rotational motion thereto, and wherein displaying a response of the first virtual element further comprises displaying a response of the first virtual element to the corresponding one of the translational motion and the rotational motion.

Example Embodiment 14

The method of any preceding or subsequent example embodiment, or combinations thereof, wherein displaying a first virtual element display further comprises displaying the first virtual element as one of a two-dimensional image and a three-dimensional image.

Example Embodiment 15

A method for planning a procedure, wherein such a method comprises displaying a first virtual element via a display device; analyzing, via a processor, physical manipulation of a control element interface configured to correspond to the first virtual element; and displaying, in response to the analysis of the physical manipulation of the control element interface, a response of the first virtual element corresponding to the physical manipulation of the control element interface.

Example Embodiment 16

The method of any preceding or subsequent example embodiment, or combinations thereof, wherein displaying a first virtual element further comprises displaying a first virtual element comprising a surgical apparatus, the surgical apparatus including one of a dental implant and a surgical instrument configured to prepare a site on a jaw structure to receive the dental implant.

Example Embodiment 17

The method of any preceding or subsequent example embodiment, or combinations thereof, further comprising one of associating and dissociating the control element interface with the first virtual element, with a selector device operably engaged with the control element interface.

Example Embodiment 18

The method of any preceding or subsequent example embodiment, or combinations thereof, further comprising selectively displaying a second virtual element on the display device, the second virtual element being configured to interact with the first virtual element.

Example Embodiment 19

The method of any preceding or subsequent example embodiment, or combinations thereof, further comprising selectively displaying a second virtual element including a representation of a jaw structure on the display device.

Example Embodiment 20

The method of any preceding or subsequent example embodiment, or combinations thereof, wherein displaying a response of the first virtual element further comprises displaying a response of the first virtual element corresponding to one of translational motion and rotational motion imparted to the control element interface by the manipulation thereof.

Example Embodiment 21

The method of any preceding or subsequent example embodiment, or combinations thereof, wherein displaying a first virtual element further comprises displaying the first virtual element as one of a two-dimensional image and a three-dimensional image.

Example Embodiment 22

A system comprising processing circuitry operatively coupled with a control element interface, wherein the processing circuitry is configured to cause the system to at least display a first virtual element on a display device; analyze physical manipulation of a control element interface configured to correspond to the first virtual element; and display, in response to physical manipulation of the control element interface, a response of the first virtual element corresponding to the physical manipulation of the control element interface.

Example Embodiment 23

The system of any preceding or subsequent example embodiment, or combinations thereof, wherein the processing circuitry is further configured to cause the system to display a first virtual element comprising a surgical apparatus, the surgical apparatus including one of a dental implant and a surgical instrument configured to prepare a site on a jaw structure to receive the dental implant.

Example Embodiment 24

The system of any preceding or subsequent example embodiment, or combinations thereof, wherein the processing circuitry is further configured to cause the system to direct the controller device to one of associate and dissociate the control element interface with the first virtual element, with a selector device operably engaged with the control element interface.

Example Embodiment 25

The system of any preceding or subsequent example embodiment, or combinations thereof, wherein the processing circuitry is further configured to cause the system to selectively display a second virtual element on the display device, the second virtual element being configured to interact with the first virtual element.

Example Embodiment 26

The system of any preceding or subsequent example embodiment, or combinations thereof, wherein the processing circuitry is further configured to cause the system to selectively display a second virtual element including a representation of a jaw structure on the display device.

Example Embodiment 27

The system of any preceding or subsequent example embodiment, or combinations thereof, wherein the processing circuitry is further configured to cause the system to display a response of the first virtual element corresponding to one of translational motion and rotational motion imparted to the control element interface by the manipulation thereof.

Example Embodiment 28

The system of any preceding or subsequent example embodiment, or combinations thereof, wherein the processing circuitry is further configured to cause the system to display the first virtual element as one of a two-dimensional image and a three-dimensional image.

Example Embodiment 29

A computer program product comprising at least one non-transitory computer readable storage medium having computer readable program instructions stored thereon, the computer readable program instructions comprising program instructions which, when executed by at least one processor implemented on a system for planning a procedure, cause the system to perform a method, wherein such a method comprises displaying a first virtual element via a display device; analyzing, via a processor, physical manipulation of a control element interface configured to correspond to the first virtual element; and displaying, in response to the analysis of the physical manipulation of the control element interface, a response of the first virtual element corresponding to the physical manipulation of the control element interface.

Example Embodiment 30

The computer program product of any preceding or subsequent example embodiment, or combinations thereof, wherein displaying a first virtual element further comprises displaying a first virtual element comprising a surgical apparatus, the surgical apparatus including one of a dental implant and a surgical instrument configured to prepare a site on a jaw structure to receive the dental implant.

Example Embodiment 31

The computer program product of any preceding or subsequent example embodiment, or combinations thereof, wherein the computer readable program instructions comprises program instructions which, when executed by the at least one processor implemented on the system, causes the system to perform a method further comprising one of associating and dissociating the control element interface with the first virtual element, with a selector device operably engaged with the control element interface.

Example Embodiment 32

The computer program product of any preceding or subsequent example embodiment, or combinations thereof, wherein the computer readable program instructions comprises program instructions which, when executed by the at least one processor implemented on the system, causes the system to perform a method further comprising selectively displaying a second virtual element on the display device, the second virtual element being configured to interact with the first virtual element.

Example Embodiment 33

The computer program product of any preceding or subsequent example embodiment, or combinations thereof, wherein the computer readable program instructions comprises program instructions which, when executed by the at least one processor implemented on the system, causes the system to perform a method further comprising selectively displaying a second virtual element including a representation of a jaw structure on the display device.

Example Embodiment 34

The computer program product of any preceding or subsequent example embodiment, or combinations thereof, wherein displaying a response of the first virtual element further comprises displaying a response of the first virtual element corresponding to one of translational motion and rotational motion imparted to the control element interface by the manipulation thereof.

Example Embodiment 35

The computer program product of any preceding or subsequent example embodiment, or combinations thereof, wherein displaying a first virtual element further comprises displaying the first virtual element as one of a two-dimensional image and a three-dimensional image.

These and other features, aspects, and advantages of the present disclosure will be apparent from a reading of the following detailed description together with the accompanying drawings, which are briefly described below. The present disclosure includes any combination of two, three, four, or more features or elements set forth in this disclosure, regardless of whether such features or elements are expressly combined or otherwise recited in a specific embodiment description herein. This disclosure is intended to be read holistically such that any separable features or elements of the disclosure, in any of its aspects and embodiments, should be viewed as intended, namely to be combinable, unless the context of the disclosure clearly dictates otherwise.

It will be appreciated that the summary herein is provided merely for purposes of summarizing some example aspects so as to provide a basic understanding of the disclosure. As such, it will be appreciated that the above described example aspects are merely examples and should not be construed to narrow the scope or spirit of the disclosure in any way. It will be appreciated that the scope of the disclosure encompasses many potential aspects, some of which will be further described below, in addition to those herein summarized. Further, other aspects and advantages of such aspects disclosed herein will become apparent from the following detailed description taken in conjunction with the accompanying drawings which illustrate, by way of example, the principles of the described aspects.

BRIEF DESCRIPTION OF THE SEVERAL VIEWS OF THE DRAWING(S)

Figure 2A:
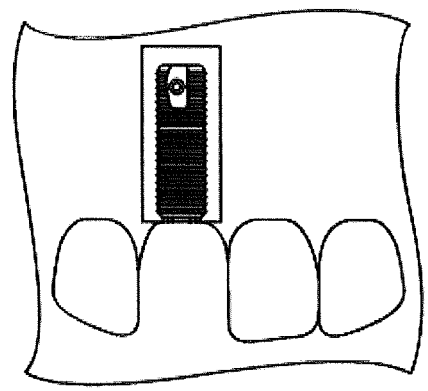
Figure 2B:
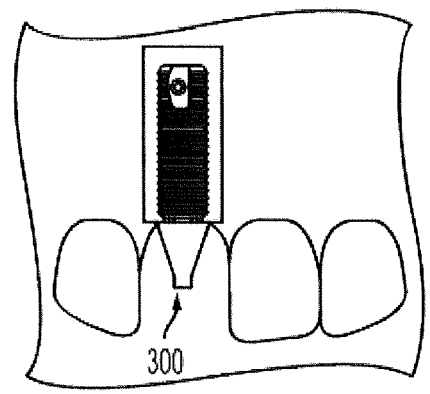
Figure 2C:
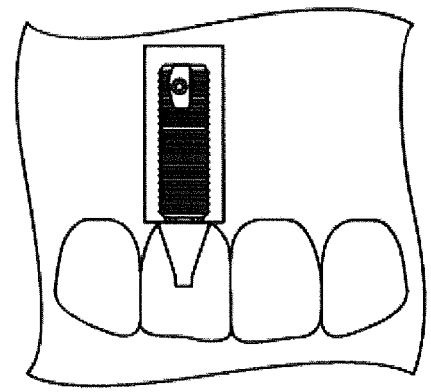
Figure 3:
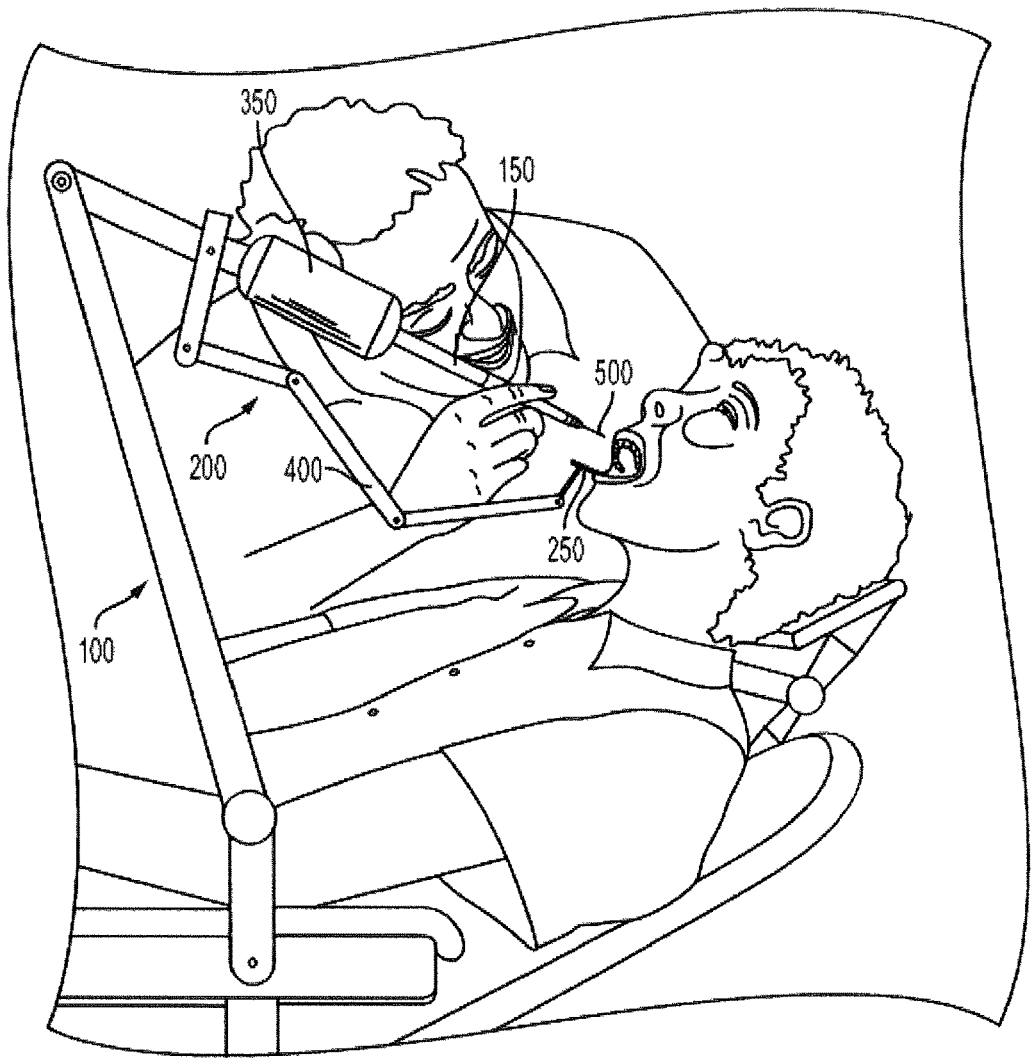
Figure 4:
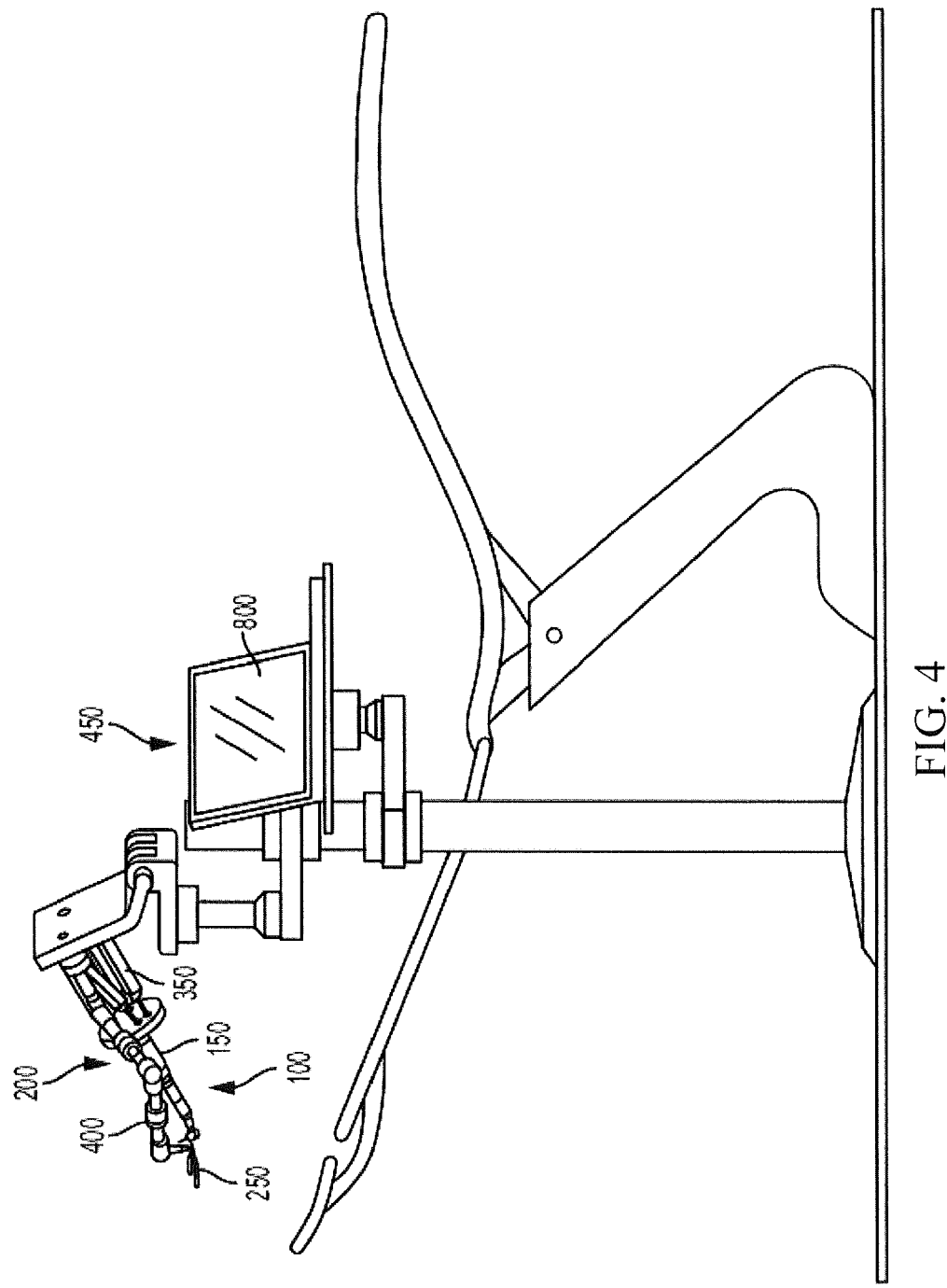
Figure 5:
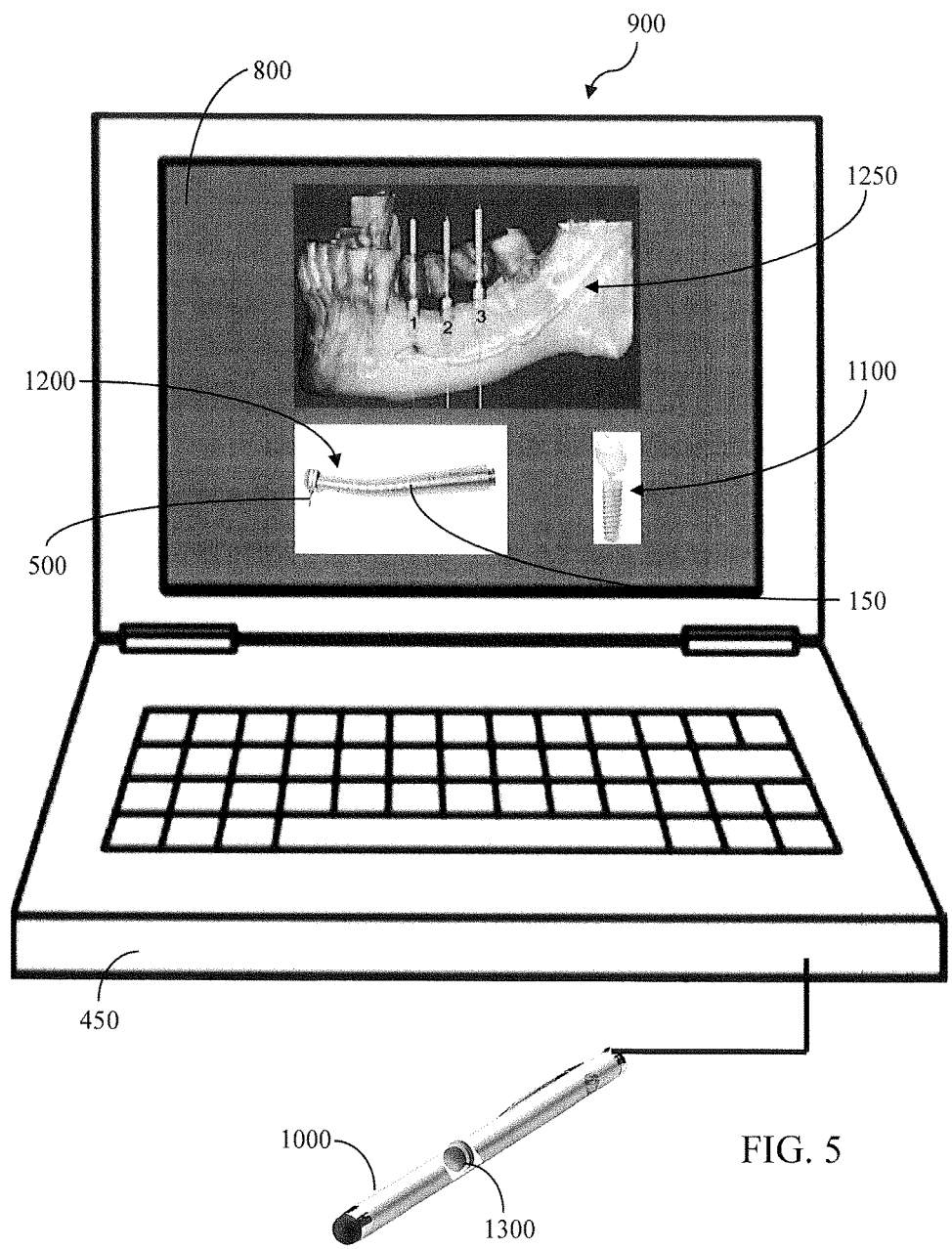
Figure 6:
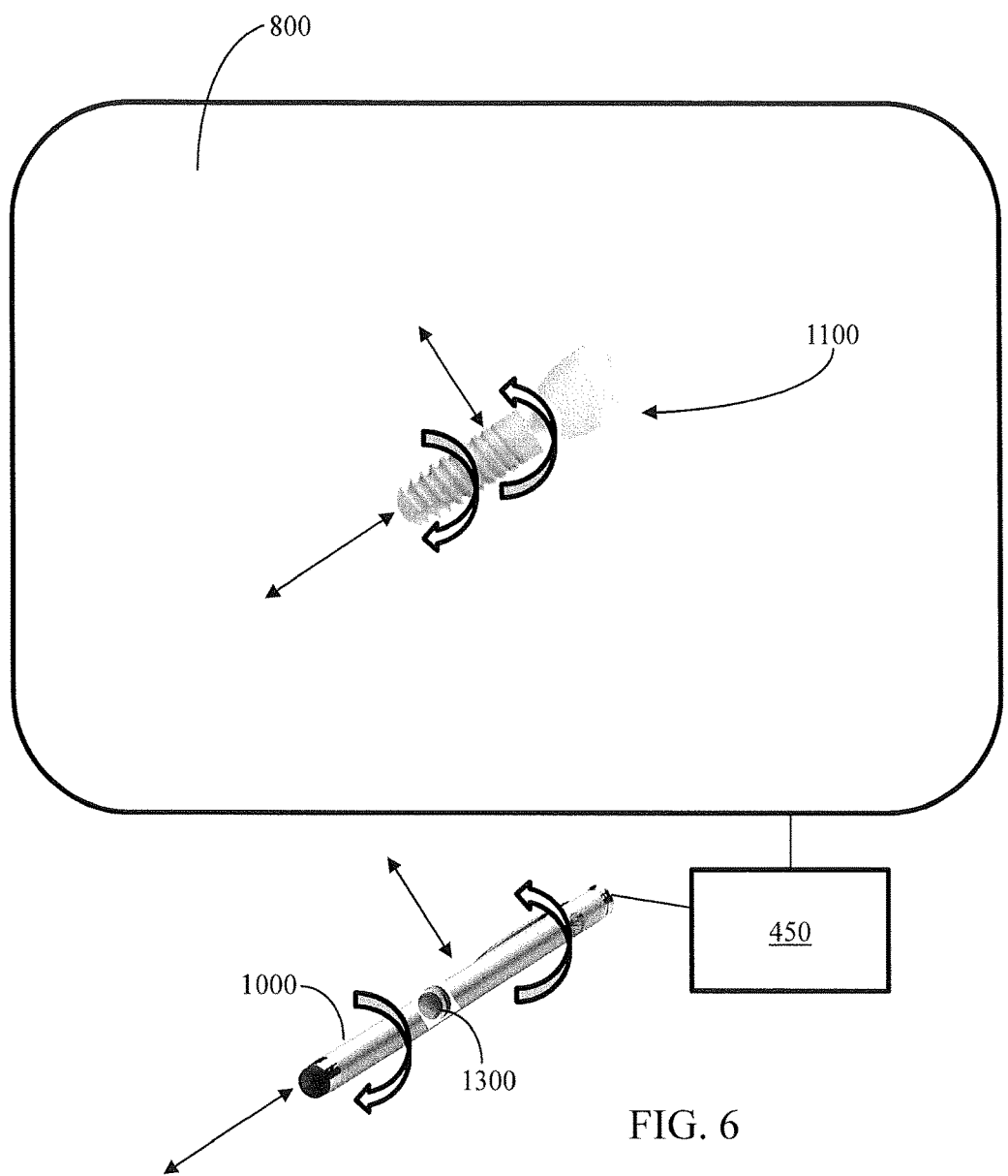
Figure 7:
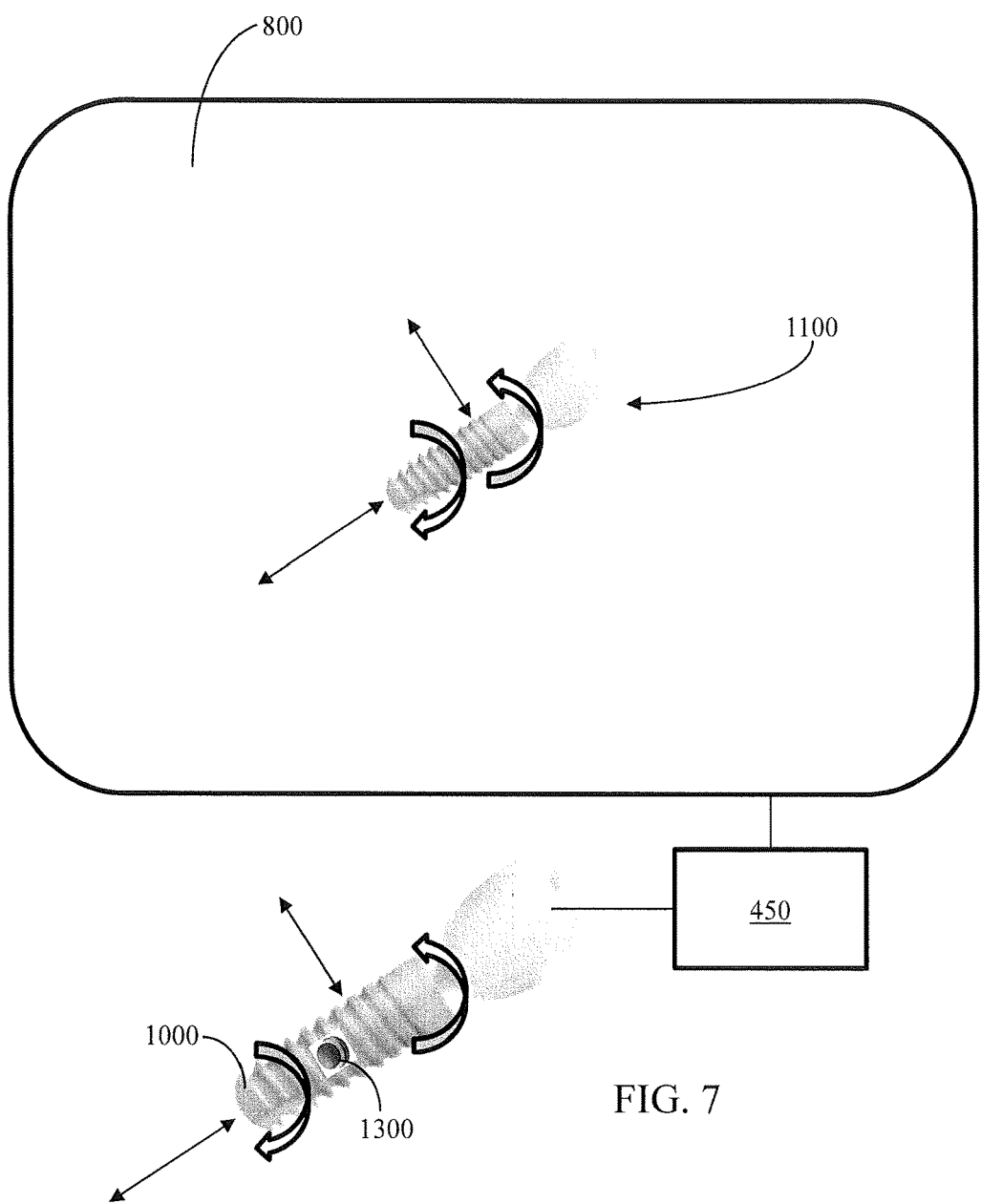

Having thus described the disclosure in general terms, reference will now be made to the accompanying drawings, which are not necessarily drawn to scale, and wherein:

FIG. 1 illustrates a prior art example of a computerized surgical planning system operating in a three-dimensional environment using a conventional pen-like stylus;

FIGS. 2A-2C schematically illustrate a dental implantation procedure with respect to the mouth of a patient;

FIGS. 3 and 4 schematically illustrate a dental implantation system, according to various aspects of the present disclosure;

FIG. 5 schematically illustrates a planning device/arrangement of a dental implantation system, according to one aspect of the present disclosure;

FIG. 6 schematically illustrates a planning device/arrangement of a dental implantation system, according to one aspect of the present disclosure, wherein physical manipulation of a control element is displayed on a display device as a corresponding response to the manipulation of a virtual element corresponding to the configuration of the control element; and FIG. 7 schematically illustrates a planning device/arrangement of a dental implantation system, according to one aspect of the present disclosure, wherein the control element is configured as a corresponding representation of a virtual element displayed on a display device.

DETAILED DESCRIPTION OF THE DISCLOSURE

The present disclosure now will be described more fully hereinafter with reference to the accompanying drawings, in which some, but not all aspects of the disclosure are shown. Indeed, the disclosure may be embodied in many different forms and should not be construed as limited to the aspects set forth herein; rather, these aspects are provided so that this disclosure will satisfy applicable legal requirements. Like numbers refer to like elements throughout.

Various aspects of the present disclosure may be at least partially based on a guided surgical robotic system and method such as that disclosed, for example, in U.S. Pat. No. 8,808,000 to Salcedo et al. and assigned to Neocis, also the assignee of the present application. The disclosure of U.S. Pat. No. 8,808,000 to Salcedo et al. is thus incorporated by reference herein.

In this regard, a dental implantation procedure generally involves an invasive incision into the gum of the patient in order to allow the practitioner to view the underlying jawbone structure. A hole is then drilled into the jawbone structure, into which a dental implant is placed (see, e.g., FIG. 2A). In some instances, the dental implant may be shaped, for example, like a screw or other threaded member. Once the dental implant is inserted into the jawbone structure, an external post is attached to the dental implant (see, e.g., FIG. 2B), and a prosthetic cap (i.e., a crown or tooth reproduction) attached to the post (see, e.g., FIG. 2C). With computerized tomography (CT) and other imaging scans becoming more common, the practitioner may be able to graphically visualize the jawbone structure, without or before the invasive incision. However, the alignment of the dental implant with respect to the jawbone structure and/or relative to other implants or teeth may be an important factor in determining, for example, the life of the dental implant, the appearance thereof, and the comfort to the patient. If the dental implant is poorly or otherwise not optimally placed, the dental implant can undesirably fail (or at least have a shorter service life), may undesirably cause other teeth or dental implants to be compromised, and/or damage proximal nerves.

FIGS. 3 and 4 thus illustrate various aspects of a dental implantation system according to the present disclosure, the system being generally indicated by the numeral 100. As previously indicated, current dental implantation procedures generally involve an imaging step, wherein CT or other appropriate images of the patient's jaw structure are obtained, and any anomalies diagnosed (i.e., whether the patient requires bone grafts to prepare the implant area). The practitioner then corrects any anomalies and proceeds with the invasive implant procedure based on the conditions associated with the patient's jaw structure, once the appropriate incisions have been made in the patient's gum. In this regard, one skilled in the art will appreciate that, though the present disclosure provides some exemplary aspects of the various systems and methods implemented with respect to the jaw structure of a patient, the various systems and method disclosed herein may be readily applicable, or otherwise readily adaptable, to other surgical procedures that are proximal to or otherwise capable of being correlated with the fiducial marker associated with the engagement between a splint or other engaging member, and the jaw structure of the patient, as otherwise disclosed herein (i.e., brain surgery, skull surgery, ENT surgery, or any other surgical procedure associated with the head/skull structure of the patient).

A dental implantation system 100 according to various aspects of the present disclosure addresses particular subjective aspects of current dental implantation procedures by providing a guided patient-interacting device 150 (otherwise referred to herein as a "cutting device" or "drilling device" or "site preparation device" or "implantation device" depending on the particular instrument 500 engaged with the patient-interacting device 150 so as to configure the patient-interacting device 150 for a particular corresponding purpose or procedure) configured to be guided with respect to the invasive portion, or at least the patient-interacting portion, of the dental implant procedure (i.e., to "prepare" the site within or otherwise engage the patient's mouth). That is, the patient-interacting device 150 is operably engaged with a guiding device 200, such as, for example, an articulating arm member 350 (i.e., a robotic arm). The guiding device 200 is adapted to operably engage or otherwise be in communication with the mouth of the patient, for example, by way of a splint 250 or other engaging member, forming or otherwise defining a fiducial marker. That is, in one instance, the splint 250 is configured to engage the patient's mouth in a "firm" or secure interaction (i.e., the splint 250 is engaged with the patient's teeth and does not move with respect to the patient's mouth). Since the splint 250 does not move with respect to the patient's mouth, the disposition of the splint 250 is known, and thus can be configured to provide a fiducial marker (i.e., a known origin or coordinate formed by the secure interaction with or otherwise associated with or attached to the splint 250) which can be used, for instance, to guide the patient-interacting device/instrument, via the guiding device 200, to prepare the site in the patient's mouth in association with the dental implant 300 (see, e.g., FIG. 2B).

In one aspect, the splint 250 is configured to be "universally applicable" (i.e., capable of forming the secure engagement with the mouth of any patient), or at least applicable across a particular range of patients (i.e., one size fits a certain size or age of patient). In order to determine a reference associated with the fiducial marker, according to one aspect of the disclosure, the splint 250 may be engaged with the patient's teeth, and the patient's jawbone structure then imaged using, for example, CT or any other suitable imaging technique such as, for instance, MRI. The fiducial marker can thus be established, for instance, as a reference origin of a relative coordinate system.

One skilled in the art will appreciate that the splint 250 may be configured in many different manners to accomplish the desired function as discussed herein. For example, the splint 250 may be rigidly attached to the patient's mouth in an appropriate manner depending on the condition of the patient. That is, if the patient has some strong teeth capable of supporting the splint 250, the splint 250 can be attached to the teeth with an adhesive or with a suitable clamp. For edentulous patients (i.e., without teeth), bone pins may be drilled through the splint 250 and into the patient's jawbone structure to fasten the splint 250 securely into place. The splint 250 may also be attached to the jawbone structure of any patient using, for example, appropriate bone screws. In one aspect, the positioning of the splint 250 with respect to the patient's mouth may not be critical or important, as long as the splint 250 remains rigidly in place. A fiducial marker (not shown) may then be formed by the secure engagement, or may otherwise be attached to, or incorporated into, or associated with the splint 250, wherein the fiducial marker may be configured to have a geometry or other characteristic or feature that uniquely defines the fiducial marker in a three-dimensional space (i.e., such that the fiducial marker is readily identified in images of the patient's jawbone structure, or is otherwise detectable and trackable using a mechanical arrangement, an electrical arrangement, an electromechanical arrangement, an optical arrangement, a magnetic arrangement, or any other suitable detection/tracking arrangement, or combination thereof). In such instances, the fiducial marker may be comprised of, for example, a radiopaque material that can be clearly defined in the image obtained, e.g., by CT or MRI.

In one aspect, the patient-interacting device 150 may be engaged with the guiding device 200, for example, in the form of an articulating arm member or a robotic arm 350, which is configured to determine a range of motion of the patient-interacting device 150/instrument 500 (i.e., translation in a particular direction (horizontal and/or vertical), and/or rotation about an axis). In some instances, the functionality of the guiding device 200 may be included in the configuration and arrangement of the articulating arm member 350, itself. For example, the articulating arm member 350 or portions thereof may include or be engaged with one or more actuators configured and arranged to cooperate to guide a distal end of the articulating arm member 350 in a desired direction and orientation, upon manipulation by the user to accomplish the surgical procedure.

In some instances, the guiding device 200 may further comprise a communication element 400 in communication between the splint 250 and the patient-interacting device 150 and/or between the splint 250 and the arm member 350. For example, the communication element 400 may comprise a mechanical linkage connecting the splint 250 to the patient-interacting device 150 or to the arm member 350. That is, the communication element 400 may comprise, for example, a mechanically- or physically-tracked arm which attaches to the splint 250 engaged with the patient. In some instances, the arm (communication element 400) may be attached to the splint 250 (rigidly and in a known, repeatable manner) with an attachment mechanism comprising a kinematic mount (i.e., a kinematic mount may be engaged between the arm and the splint 250). Attached to the patient in this manner via the attachment mechanism and the splint 250, the communication element 400 may be tracked or otherwise monitored to provide data (whether constantly, selectively, or otherwise as necessary) about the position of the patient (i.e., with respect to the fiduciary or fiducial marker) to the patient-interacting device 150 and/or to the arm member 350, while still providing for accurate guidance of the patient-interacting device 150 and/or the arm member 350, in the event that the patient moves during the surgical procedure.

However, one skilled in the art will appreciate that the splint 250 and/or the fiducial marker determined thereby may be communicated to the patient-interacting device 150 and/or to the arm member 350 in many different manners. For example, instead of or in addition to the physical arm (communication element 400), the fiducial marker may be communicated via a communication element 400 comprising a wireless transceiver, a hardwire connection, an optical communication system (i.e., a camera or other video device), an acoustic tracking system, or any other suitable mechanism, whether electrical, mechanical, electromechanical, acoustic, or optical in nature. That is, in various instances, the kinematic mount, itself, may comprise an attachment point for a tracking portion (and/or the tracking arm or other tracking provision) associated with the guidance system for the surgical robot (i.e., wherein, for instance, reflective markers may be mounted to the attachment point for optical tracking of the fiducial marker or the splint device itself, or the attachment point may include a securing site for forming a mechanical connection therewith for mechanical tracking of the fiducial marker, or the attachment point may otherwise be configured to receive an appropriate element associated with any other suitable tracking arrangement for the fiducial marker, whether electrical, mechanical, electromechanical, acoustic, or optical in nature). In other aspects, the kinematic mount may be configured or otherwise arranged to function as a fixed mounting site for particular tracking devices such as, for example, one or more markers that may be permanently affixed to the kinematic mount 500 and configured to be trackable by an optical-type tracking device (i.e., an optical tracking marker).

In any instance, the system 100 may be further configured to include a controller device 450 (i.e., a computer device as shown in FIG. 4) for determining, controlling, or tracking the fiducial marker with respect to the image of the patient's mouth having the splint 250 disposed therein. The controller device 450 may also be configured and arranged to appropriately communicate the fiducial marker to the patient-interacting device 150 and/or to the arm member 350. In some aspects, the system 100 or the controller device 450 may also comprise a planning device or otherwise include planning functionality for allowing a user to develop the virtual implantation plan, as otherwise disclosed herein, in conjunction with the hardware and/or software of the system 100.

In one aspect, the controller device 450 may be further configured to receive the image of the patient's jawbone structure (having the splint 250 therein). In some instances, the controller device 450, which includes a processor, may be further configured to be capable of executing a planning routine that may comprise software, hardware, or a combination thereof (i.e., a planning device and/or planning functionality). The planning routine thus allows the practitioner to create, for example, a virtual implantation plan based on the captured image(s), whether in two dimensions or three dimensions, and to manipulate the image(s) of the patient's jawbone structure in conjunction with a "virtual implant" in order to develop the virtual implantation plan or placement determination of the prosthesis for the patient, in conjunction with a computerized model based on the image(s). In some aspects, the planning routine, virtual implantation plan, and/or placement determination may be created in relation, for example, to a coordinate system (relative or absolute), as will be appreciated by one skilled in the art, configured to associate the planning parameters with the fiducial marker. In other aspects, the controller device 450 and/or the planning device associated therewith may include a peripheral device (i.e., a trackball or joystick in conjunction with, for example, 3D goggles, all not shown) to assist with or otherwise permit virtual manipulation of the placement of the virtual implant(s) with respect to the image(s) of the patient's jaw structure in order to, for example, align the implant(s) relative to each other or relative to adjacent teeth, to align the implant(s) relative to the affected nerve, and/or to align the implant(s) relative to the jawbone structure. The controller device 450 and/or the planning device may be further configured to perform such manipulation manually, automatically, or semi-automatically, as necessary or desired. Because the virtual implant(s) may be manipulated in a similar manner to the image(s), the orientation or placement of the virtual implant(s) may represent the desired actual placement of the implant with respect to the patient's jawbone structure, thus providing an intuitive interface for planning the implantation procedure.

In aspects where the splint 250/fiducial marker approach is used, the patient is automatically registered with the system 100/controller device 450 once the communication element 400 is attached to or otherwise engaged or in communication with the splint 250 via the kinematic mount of the attachment mechanism. That is, the fiducial marker is automatically determined from the image(s) of the patient's jawbone structure, and the alignment and location thereof in physical space is known due to the kinematic mount connecting the communication element 400 (i.e., arm) to the splint 250. One skilled in the art will appreciate, however, that other alignment approaches may be implemented that do not necessarily require a fiducial marker. For example, in some instances, a surface matching technique can be implemented. More particularly, the patient's jawbone structure may be manipulated into a 3D configuration in the captured image(s). A suitable scanning device (i.e., a physical pointer or other imaging device such as an ultrasound transducer or OCT (optical coherence tomography) scanner may be attached to an end effector (i.e., tip) of the arm member 350 such that the tip of the arm member 350 is capable of scanning the patient's jawbone structure to "surface match" the captured and manipulated image(s) with an actual scan of the jawbone structure, as administered, for example, via the controller device 450.

One skilled in the art will further appreciate that the association of the fiducial marker with the patient's anatomy, via the controller device 450, may be accomplished in different manners. For example, with respect to the registration of the image (e.g., CT scan) to the fiducial marker, one method could involve the jaw structure of the patient being imaged with the fiducial marker in place, as previously discussed, wherein the patient would then be substantially immediately subjected to the implantation procedure. Such a scheme may be beneficial, for example, in reducing the number of visits to the practitioner by the patient. However, in some instances, the practitioner may not have the imaging capabilities at hand, or may prefer to carefully determine the virtual implantation plan before carrying out the implantation procedure. In both such instances, the patient will likely be required to return to the practitioner at a later time. Accordingly, in such situations, a pre-operative imaging procedure (e.g., CT scan) may be performed on the jaw structure of the patient, without a fiducial marker in place (i.e., a "normal" scan by which the practitioner can determine the virtual implantation plan). This pre-operative imaging procedure can thus be performed, for example, at the practitioner's site, or at a dedicated scanning/imaging center. Subsequently, immediately prior to the implantation procedure being performed, and with the fiducial marker(s) engaged with the jaw structure of the patient, the practitioner may capture another image (e.g., CT scan, panoramic x-ray, or two single x-rays) of the patient's jaw structure. The controller device 450/planning device may thus also be configured to correlate the pre-operative image (used to determine the virtual implantation procedure) with the "day of" image so as to register the fiducial marker(s) with respect to the original pre-operative image. Such a registration or correlation procedure may be implemented in hardware, software, or a combination thereof, as will be appreciated by one skilled in the art. The implantation procedure could then proceed as otherwise disclosed herein.

In any instance, the communication element 400 may be configured to communicate with the arm member 350 in a manner known to the system 100, such that the position/movement characteristics of the end effector/tip thereof are also known. This engagement between the communication element 400 and the arm member 350 thus allows the patient-interacting device 150/instrument 500 (i.e., the end effector/tip) to be registered with respect to the fiducial marker (or other reference with respect to the patient) attached to the patient via the splint 250, the kinematic mount, the communication element 400, and the arm member 350. In this manner, the virtual implantation process, planned through the controller device 450/planning device, may be accomplished in relation to the fiducial marker (or other reference with respect to the patient) and thus translated or otherwise communicated to the system 100 for directing the patient-interacting device 150/instrument 500 via the guiding device 200 and the arm member 350. As previously disclosed, and as will be appreciated by one skilled in the art, the communication element 400 may, in some instances, be configured to communicate between the splint 250/kinematic mount and the controller device 450/planning device (and/or between the splint 250/kinematic mount and the patient-interacting device 150/instrument 500), based upon the premise of establishing a known association of the fiducial marker with the patient's anatomy, in relation to which the guiding device 200 is used to guide the patient-interacting device 150/instrument 500 via the arm member 350 during the implantation procedure.

The patient-interacting device 150/instrument 500 may comprise, be disposed in, or otherwise engaged with the end effector of the arm member 350 (robotic arm). The arm member 350 may be configured, for example, to provide six degrees of freedom and can also be configured to restrict or otherwise control the movement of the patient-interacting device 150/instrument 500. Further, in some instances, the arm member 350 may have a miniature parallel structure to which the patient-interacting device 150 is secured and allowed to have full freedom of movement when not in cutting/preparation/implantation mode. Since the patient-interacting device 150/instrument 500 comprises or is attached to the end effector of the arm member 350, the patient interacting portion (i.e., the cutting/drilling tip) is the instrument 500 (see, e.g., FIG. 3) of the patient-interacting device 150, and the instrument 500 thus must be in a known position (i.e., known to the system 100/controller device 450) relative to the arm member 350. In some aspects, in order to calibrate the interacting portion/instrument 500 of the patient-interacting device 150 with respect to the fiducial marker, a calibration element may be engaged with the patient-interacting device 150 via a kinematic coupling (i.e., rigidly mounted thereto in a known, repeatable manner). One skilled in the art will thus appreciate that the interacting portion/instrument 500 of the patient-interacting device 150 can then be calibrated with various tip calibrating methods (i.e., invariant point, etc.). Once calibrated, the calibration element is replaced with a cutting/drilling element (instrument 500) in the patient-interacting device 150, in a known and repeatable manner, so that the calibration parameters (i.e., the position of the distal-most point and axis of cutting/drilling) associated with the interacting portion/instrument 500 are maintained as calibrated.

With the alignment with respect to the patient established and known by the system 100/controller device 450, and the virtual implantation plan developed through the controller device 450/planning device, the implantation procedure (i.e., cutting/drilling/insertion) can then be initiated by the practitioner moving the patient-interacting device 150/instrument 500 toward the patient's mouth (having the splint 250 engaged therewith). In such instances, the controller device 450/planning device is configured to control, restrict, or otherwise modulate the movement of (or the practitioner's ability to move) the patient-interacting device 150 via the arm member 350 such that the action of the practitioner merely moves the interacting portion/instrument 500 (i.e., the cutting/drilling element) to the appropriate starting position for the implantation procedure, with respect to the patient's jawbone structure, as determined by the controller device 450/planning device and dictated by the virtual implantation plan. Once the cutting/drilling element is in the position dictated by the controller device 450/planning device, the invasive portion of the procedure can then be initiated, wherein the controller device 450/planning device may further dictate other parameters of the implantation device 150/instrument 500 such as, for example, the orientation of the path of the cutting/drilling element (instrument 500) and the cutting/drilling distance along that path from the cutting/drilling origin, also according to the virtual implantation plan. In some instances, the system 100 disclosed herein may be configured such that the patient-interacting device 150 is not guided by the practitioner, but is only urged by the practitioner along a procedural route determined via the virtual implantation plan and implemented via the controller device 450/planning device and the arm member 350. That is, the system 100 may be configured to restrict the practitioner to performing the implantation procedure with respect to the patient, as determined via the virtual implantation plan and implemented via the controller device 450/planning device and the arm member 350, whereby the controller device 450/planning device controls the allowable movement of the arm member 350 (and thus the patient-interacting device 150/instrument 500) in accordance with the virtual implantation plan created from the image(s) of the patient's jawbone structure. For instance, the system 100 may be configured for restricted movement of the arm member 350/patient-interacting device 150/instrument 500, as communicated to the practitioner through tactile/haptic feedback, where, for example, the arm member 350/patient-interacting device 150/instrument 500 may be easier to move according to the virtual implantation plan, and more difficult to move if deviating from the virtual implantation plan.

One skilled in the art will also appreciate, however, that the physical structure of the arm member 350/patient-interacting device 150/instrument 500 may not necessarily be configured to provide full and absolute controlled movement according to the virtual implantation plan (i.e., due to vibration, flexing of components, gravity, and/or excessive force applied by the practitioner) and, as such, the system 100/controller device 450 may be further configured to provide other manners of feedback to the practitioner such as, for example, via a deviation warning indicia, haptic feedback, or any other suitable audio and/or visual and/or any other suitable mechanism. Therefore, the system 100/controller device 450 includes provisions for actually implementing the virtual implantation plan, and thus facilitates a more accurate implantation procedure, rather than merely warning the practitioner if any procedural parameters may be inaccurate. One skilled in the art will also appreciate, however, that, in some instances, the system 100 may be further configured to autonomously accomplish the virtual implantation plan, without the manipulation of the practitioner, through automatic manipulation of the arm member 350/patient-interacting device 150/instrument 500 via the controller device 450/planning device.

In one exemplary surgical procedure using a dental implantation system 100, as disclosed herein, the splint 250 (i.e., mouthpiece) is first attached to the patient's teeth, and thus provides or is associated with a fiducial marker. The patient's jawbone structure is then imaged (with the splint 250 in place and engaged with the patient's teeth) using, for example, CT or any other appropriate imaging technique (e.g., MRI), and the image(s) communicated to the controller device 450. The controller device 450 may be further configured to be capable of executing an implantation routine, thus allowing the practitioner to develop an implantation plan for the patient, for example, by manipulating a virtual implant with respect to the captured image(s). Once the virtual implantation plan is created, the communication element 400 is engaged with (i.e., attached to the patient's mouth, with the patient being positioned in a suitable position to initiate the procedure) or otherwise placed into communication with the splint 250 (i.e., via the kinematic mount). The arm member 350, patient-interacting device 150, and interacting portion/instrument 500 thereof, are then calibrated by the practitioner (or automatically by the controller device 450), before the actual cutting/drilling element (instrument 500) of the patient-interacting device 150 is used by the practitioner (or autonomously via the controller device 450/planning device), via the patient-interacting device 150 as guided by the arm member 350 and the controller device 450, to accomplish the implantation procedure as planned and dictated by the virtual implantation plan.

In some aspects, as previously discussed, the controller device 450, which includes a processor, may be configured to be capable of executing a planning routine or procedure that may comprise software, hardware, or a combination thereof (i.e., a planning device, planning arrangement, and/ or planning functionality). The planning routine thus allows the practitioner to create, for example, a virtual implantation plan based on the captured image(s) of the patient's jawbone structure, whether in two dimensions or three dimensions, and to manipulate the image(s) of the patient's jawbone structure in conjunction with a "virtual implant" in order to develop the virtual implantation plan or placement determination of the prosthesis for the patient, in conjunction with a computerized model based on the image(s) (i.e., wherein the virtual planning procedure could be displayed to the user on a display or display device 800 associated or otherwise in communication with the controller device 450). In some aspects, the planning routine, virtual implantation plan, and/or placement determination may be created in relation, for example, to a coordinate system (relative or absolute), as will be appreciated by one skilled in the art, configured to associate the planning parameters with the fiducial marker. In further aspects, the planning routine may also involve manipulation of the surgical instrument(s) to be used in performing the dental implant procedure, for example, as an instructional or training tool via the display device 800.

In other aspects, as shown, for example, in FIG. 5, the controller device 450 and/or the planning device/arrangement 900 associated therewith may include a peripheral device or control element 1000 (i.e., a trackball, joystick, or stylus, in conjunction with, for example, 3D goggles (as shown, for example, in FIG. 1)) to assist with or otherwise permit virtual manipulation of the placement of the virtual implant(s) with respect to the image(s) of the patient's jaw structure in order to, for example, align the implant(s) relative to each other or relative to adjacent teeth, to align the implant(s) relative to the affected nerve, to align the implant(s) relative to the jawbone structure, and/or otherwise to perform a "test fitting" of the implant(s). In some instances, the control element 1000 may be implemented to assist with or otherwise permit virtual manipulation of the surgical device (i.e., the patient-interacting device 150/instrument 500) with respect to the implantation site, for instance, as a teaching or training tool. In yet other aspects, the peripheral device or control element 1000 may be more generally configured to correspond to a first virtual element 1000 which, in some instances, may broadly comprise a surgical apparatus, wherein such a surgical apparatus may include one of a dental implant, a surgical instrument configured to prepare a site on a jawbone structure to receive the dental implant, or any other appropriate apparatus associated with a surgical procedure, whether dental-related or not.

As also previously discussed, however, if the peripheral device/control element 1000 is implemented in a "conventional manner" (i.e., to click, drag, and drop like a conventional mouse or similarly with a conventional stylus), such an arrangement may not necessarily be intuitive, ergonomically agreeable, or convenient for a user to manipulate a virtual object, such as a dental implant or surgical instrument, in a two-dimensional or three-dimensional virtual environment, whether or not the user is significantly experienced with the system, while viewing such manipulation on the display device 800.

As such, since the orientation and/or placement of the virtual implant (i.e., a first virtual element 1100) may represent the desired actual placement of the implant with respect to the patient's physical jawbone structure, or since the manipulation of a virtual surgical instrument can represent the actual use of that surgical instrument with respect to the patient's physical jawbone structure, aspects of the present disclosure are directed to a system for planning a procedure (i.e., a planning device/arrangement 900), wherein the display device 800 is configured to display the first virtual element 1100 (i.e., a dental implant comprising an implant element and a prosthetic member, or a surgical instrument represented by the patient-interacting device 150/instrument 500). The controller device 450, having a processor, is configured to be in communication with the display device 800, wherein the controller device 450 is further configured to direct the display device 800 to display the first virtual element 1100. In such aspects of the present disclosure, the physical control element 1000, in communication with the controller device 450, may be particularly configured to correspond to the first virtual element 1100. As such, in particular aspects, an actual or physical manipulation of the control element 1000 by the user is displayed (i.e., via cooperation between the processor of the controller device 450, the control element 1000, and the display device 800) on the display device 800, wherein the actual manipulation of the physical control element 1000 by the user is manifest and represented by a response of the first virtual element 1100 displayed on the on display device 800, as if the first virtual element 1100 was subjected to the actual manipulation of the control element 1000. One skilled in the art will appreciate that such aspects are fundamentally different from manipulating a virtual object on a display device in a conventional manner using, for example, a mouse/keyboard or stylus pointer. In particular aspects, the correlation/contemporaneousness between the manipulation of the control element 1000 and the response of the first virtual element 1100 displayed on the display device 800 may be arranged to occur in real time or substantially real time, such that the immediacy of the response of the first virtual element 1100 to the manipulation of the physical control element 1000 is apparent to the user.

For example, as shown in FIG. 6, if the first virtual element 1100 was configured as a threaded post (i.e., a dental implant configured as a threaded screw for forming a threaded engagement with a bore formed in the patient's jawbone structure), the control element 1000 may be generally configured as an elongate member (i.e., a stylus), but may also be specifically configured as a threaded screw, or configured as any suitable corresponding object representative of a threaded screw (see, e.g., FIG. 7). Such a threaded post, in its actual functionality, must be rotated about the longitudinal axis thereof in order to form the threaded engagement, and the virtual representation thereof thus retains the same functionality for the planning purposes disclosed herein. As such, the control element 1000 (i.e., the stylus) may be configured to cooperate with the controller device 450 such that actual rotation of the stylus (control element 1000) about the longitudinal axis thereof is manifest or otherwise realized on the display device 800 as the first virtual element 1100 (i.e., the threaded post) rotating about the longitudinal axis thereof, as if it were being manipulated in the same manner as the control element 1000. Moreover, any other manipulation of the control element 1000 would be manifest and realized as a corresponding response of the first virtual element 1100. For instance, if translational motion (i.e., motion in any, all, or any combination of the x-, y-, and z-axes in a three-dimensional environment) or rotational motion (i.e., rotation about any, all, or any combination of the x-, y-, and z-axes in a three-dimensional environment) is imparted to the control element 1000, the display device 800 would display the first virtual element 1100 (i.e., the threaded post) as translating and/or rotating in the same manner as the control element 1000, as if it were being manipulated in the same manner as the control element 1000.

Such aspects can be described in different manners. For example, the control element 1000 may be arranged as a proxy for the first virtual element 1100 in regard to the manipulation of the first virtual element 1100. As such, the control element 1000 is the recipient of the manipulation or the object being manipulated, while the first virtual element 1100 displayed on the display device 800 demonstrates or otherwise reflects the response of the first virtual element 1100 to the manipulation (i.e., as if the first virtual element itself is being manipulated by the user, instead of the control element 1000). In other instances, the physical manipulation of the control element 1000 is replicated by the controller device 450 as the response of the first virtual element 1100 displayed on the display device 800. Still further, the control element 1000 may have up to six degrees of freedom (i.e., configured as a body in a three-dimensional environment, wherein the body is free to move forward/backward, up/down, left/right (i.e., translation in three perpendicular axes) combined with rotation about the three perpendicular axes (i.e., pitch, yaw, and roll), with the first virtual element 1100 correspondingly displayed to have the same degrees of freedom as the control element 1000. As such, one skilled in the art will appreciate that the control element 1000 (i.e., a physical object) is used to manipulate a corresponding virtual object (i.e., the first virtual element 1100) in the virtual environment represented by the display device 800.

In some aspects, a plurality of virtual elements may be displayed or selectively displayed (i.e., by user selection) via the controller device 450 on the display device 800. For example, in addition to the first virtual element 1100, a second virtual element 1200 (see, e.g., FIG. 5) may be displayed by the controller device 450 on the display device 800. In one instance, the first virtual element 1100 may comprise a dental implant, as previously discussed, while the second virtual element 1200 may comprise a surgical apparatus, such as a surgical instrument for performing a surgical procedure (i.e., used to prepare the site within the patient's mouth for receiving the dental implant). In such instances, a selector device 1300 may be operably engaged with the control element 1000, wherein the selector device 1300 may be configured to direct the controller device 450 to associate the control element 1000 with the first virtual element 1100 and/or the second virtual element 1200, or to dissociate the control element 1000 from the first virtual element 1100 and/or the second virtual element 1200. That is, the selector device 1300 may be used to indicate to the controller device 450 as to the virtual element displayed on the display device 800 that is to be associated with or dissociated from the control element 1000 (i.e., to establish or disestablish correspondence between the control element 1000 and one or more of the virtual elements displayed on the display device 800). In some aspects, the first virtual element 1100 and/or the second virtual element 1200 may be configured to interact with the other. For example, in some aspects, the second virtual element may comprise, for instance, a visual representation, whether in two dimensions or three-dimensions, of the patient's jawbone structure (see, e.g., element 1250 in FIG. 5). Accordingly, in such aspects, the first virtual element 1100 may be manipulated via the control element 1000 such that the first virtual element 1100 (i.e., a dental implant or a surgical instrument) interacts with the patient's jawbone structure 1250 (i.e., a second virtual element).

In particular aspects where the control element 1000 comprises, for example, a stylus, the selector device 1300 may be accomplished, for example, by contacting a tip of the stylus with the display device 800 in the portion of the display device 800 where the virtual element being selected or deselected is displayed. However, the selector device 1300 may be implemented in many different manners, as will be appreciated by one skilled in the art. In some instances, the selector device 1300 may be operably engaged with the control element 1000, and may comprise, for example, one of a touch-sensitive actuator, a pressure-sensitive actuator, an optical actuator, and an acoustic actuator, associated with the control element 1000. For example, the user's selection of a virtual element displayed on the display device 800 may be signified or otherwise actuated by way of, for example, a selector device 1300 comprising a camera, an infrared sensor, an acoustic sensor, a range-finder, or other appropriate sensor that is engaged with or in proximity to the control element 1000 to determine if an actual selection is made by the user. In other instances, for example, the selector device 1300 may comprise, for example, an appropriate pressure switch or sensor mounted on the control element 1000.

The control element 1000 and/or the selector device 1300 may be established in communication with the controller device 450 and/or other components in the system 100, for example, by way of an electrical communication system, a mechanical communication system, an electromechanical communication system, an optical communication system, and combinations thereof, or through any other suitable communication arrangement, as will be appreciated by one skilled in the art, wherein the communication system or communication arrangement may, for example, comprise a wireless communication system and/or a wired communication system.

Upon selection of the one or more virtual elements displayed on the display device 800, the controller device 450 may be further configured to establish a correlation between the attributes of the control element 1000, and the characteristics of the selected virtual element on the display device 800 (see, e.g., FIG. 6). For instance, reverting to the threaded post (i.e., dental implant) example, on selection of the virtual threaded post displayed on the display device 800, the controller device 450 may be configured to correlate the longitudinal axes of the virtual threaded post and the stylus, as well as to ascertain the orientation of each (i.e., that the engaging end of the threaded portion of the threaded post corresponds to the tip of the stylus). This correlation may be established in different manners. For example, the control element 1000 may be provided with one or more location and/or motion sensors (i.e., accelerometers or trackable location indicia incorporated in the control element 1000) that are arranged to be in communication with the controller device 450, such that the location, orientation, or other data indicative of the attributes of the control element 1000 are made known to the controller device 450 for correlation with the characteristics of the selected virtual element on the display device 800. One skilled in the art will appreciate, however, that the location, orientation, or other data indicative of the attributes of the control element 1000 may be known or otherwise determined in different manners. For instance, an optical arrangement (i.e., a stereoscopic camera or other imaging device) may be implemented to optically analyze the control element 1000, in conjunction with the controller device 450, to evaluate the location, orientation, or other data indicative of the attributes of the control element 1000 for correlation with the characteristics of the selected virtual element on the display device 800.

According to various aspects, the control element 1000 may have any suitable shape or form to be in correspondence to the selected virtual element, such that the virtual element may be moved around in the virtual environment, which tracking the movement of the control element 1000 in an actual physical environment. Moreover, the concepts disclosed herein may be extended to other instances outside of dental implant procedures. For example, in relation to preoperative planning applications, the concepts herein can be applied to any implant situation such as, for instance, knee and hip implants. Even though such implants may be significantly different from a dental implant discussed herein, a basic aspect may be applied in that a physical representation of the implant can be manipulated in actual physical space by a user, while a virtual representation of that implant is moved in the virtual environment in the same manner. In some particular aspects, any object can be, for example, printed as a scale model (i.e., using a 3D printer), and the manipulation thereof can be tracked (i.e., tracking the manipulation of the scale model could be used as the manipulation basis of the control element) to create an even more seamless interaction with the virtual representation of the object in the virtual environment (see, e.g., FIG. 7). One skilled in the art will also appreciate that such concepts may also be implemented in regard to 2D display environments (i.e., standard computer screens) as well, even in instances, where a pseudo-three-dimensional representation may be provided in that two-dimensional environment.

Many modifications and other embodiments of the inventions set forth herein will come to mind to one skilled in the art to which these disclosed embodiments pertain having the benefit of the teachings presented in the foregoing descriptions and the associated drawings. Therefore, it is to be understood that embodiments of the invention are not to be limited to the specific embodiments disclosed and that modifications and other embodiments are intended to be included within the scope of the invention. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the disclosure.

In this regard, for example, different combinations of elements and/or functions than those explicitly described above are also contemplated within the scope of the disclosure. For example, aspects of the present disclosure may provide a method for planning a procedure, comprising displaying a first virtual element via a display device; analyzing, via a processor, physical manipulation of a control element interface configured to correspond to the first virtual element; and displaying, in response to the analysis of the physical manipulation of the control element interface, a response of the first virtual element corresponding to the physical manipulation of the control element interface.

Another aspect may provide a system comprising processing circuitry operatively coupled with a control element interface, wherein the processing circuitry is configured to cause the system to at least display a first virtual element on a display device; analyze physical manipulation of a control element interface configured to correspond to the first virtual element; and display, in response to physical manipulation of the control element interface, a response of the first virtual element corresponding to the physical manipulation of the control element interface.

A further aspect may provide a computer program product comprising at least one non-transitory computer readable storage medium having computer readable program instructions stored thereon. The computer readable program instructions comprise program instructions which, when executed by at least one processor implemented on a system for planning a procedure, cause the system to perform a method comprising displaying a first virtual element via a display device; analyzing, via a processor, physical manipulation of a control element interface configured to correspond to the first virtual element; and displaying, in response to the analysis of the physical manipulation of the control element interface, a response of the first virtual element corresponding to the physical manipulation of the control element interface.

In particular aspects implementing a stylus as the control element, it may also be observed that, by the user grasping the stylus as if it was, for example, a dental implant (i.e., rather than in a conventional manner wherein the stylus is used as a pointer), the controller device can correlate the virtual representation of the dental implant with the physical attributes of the stylus, such that the virtual dental implant displayed on the display device can be manipulated by physically moving the stylus as if it was the virtual dental implant in a 3D virtual environment. In such a manner, the user in a 3D environment may now have a full 3D interactive experience by being able to visualize in real time the interactivity of the virtual dental implant in the 3D environment by moving a physical 3D object, which is similar to the virtual object being virtually represented in the 3D environment.

Although specific terms are employed herein, they are used in a generic and descriptive sense only and not for purposes of limitation. In this regard, it should be understood that although the terms first, second, etc. may be used herein to describe various steps or calculations, these steps or calculations should not be limited by these terms. These terms are only used to distinguish one operation or calculation from another. For example, a first calculation may be termed a second calculation, and, similarly, a second step may be termed a first step, without departing from the scope of this disclosure. As used herein, the term "and/or" and the "/" symbol includes any and all combinations of one or more of the associated listed items. Also, as used herein, the singular forms "a", "an" and "the" are intended to include the plural forms as well, unless the context clearly indicates otherwise. It will be further understood that the terms "comprises", "comprising", "includes", and/or "including", when used herein, specify the presence of stated features, integers, steps, operations, elements, and/or components, but do not preclude the presence or addition of one or more other features, integers, steps, operations, elements, components, and/or groups thereof. Therefore, the terminology used herein is for the purpose of describing particular embodiments only and is not intended to be limiting.

That which is claimed:

1. A system for planning a procedure, comprising:
    a display device configured to display a first virtual element, the first virtual element comprising a virtual surgical apparatus including a virtual dental implant or a virtual surgical instrument configured to prepare a site on a virtual jaw structure to receive the virtual dental implant;
    a controller device having a processor and being configured to be in communication with the display device, the controller device being further configured to direct the display device to display the first virtual element;
    a physical control element in communication with the controller device, the physical control element being configured as a corresponding scale model of the first virtual element and having six degrees of freedom of movement, wherein the processor is configured to analyze an actual manipulation and movement of the physical control element, and to apply the analysis of the actual manipulation and movement of the physical control element in each degree of freedom to virtually manipulate and move the first virtual element displayed on the display device, the virtual manipulation and movement of the first virtual element displayed on the display device being the same as the actual manipulation and movement of the physical control element; and a selector device operably engaged with the physical control element, the selector device being configured to direct the controller device to associate the physical control element with or dissociate the physical control element from the first virtual element, such that the virtual manipulation and movement of the first virtual element is the same as the actual manipulation and movement of the physical control element upon to the physical control element being associated with the first virtual element by the selector device, and such that the first virtual element is not virtually manipulated and moved upon to the physical control element being dissociated from the first virtual element.

2. The system of claim 1, further comprising a second virtual element selectively displayed by the display device, the second virtual element being configured to interact with the first virtual element.

3. The system of claim 2, wherein the second virtual element includes the virtual jaw structure.

4. The system of claim 1, wherein the actual manipulation and movement of the physical control element includes one of translational motion and rotational motion, and wherein the virtual manipulation and movement of the first virtual element displayed on the display device corresponds to and is the same as the one of translational motion and rotational motion of the physical control element.

5. The system of claim 1, wherein the display device is configured to display the first virtual element as one of a two-dimensional image and a three-dimensional image.

6. A method for planning a procedure, comprising:
displaying a first virtual element on a display device with a controller device having a processor and configured to be in communication with the display device, the first virtual element comprising a virtual surgical apparatus including a virtual dental implant or a virtual surgical instrument configured to prepare a site on a virtual jaw structure to receive the virtual dental implant;

performing an actual manipulation and movement of a physical control element, the physical control element being in communication with the controller device and being configured as a corresponding scale model of the first virtual element and having six degrees of freedom of movement;

analyzing, with the processor, the actual manipulation and movement of the physical control element, and applying the analysis to virtually manipulate the first virtual element displayed on the display device, the virtual manipulation and movement of the first virtual element displayed on the display device corresponding to and being the same as the actual manipulation and movement of the physical control element in each degree of freedom; and directing the controller device, using a selector device operably engaged with the physical control element, to associate the physical control element with or dissociate the physical control element from the first virtual element, such that the virtual manipulation and movement of the first virtual element is the same as the actual manipulation and movement of the physical control element upon to the physical control element being associated with the first virtual element by the selector device, and such that the first virtual element is not virtually manipulated and moved upon to the physical control element being dissociated from the first virtual element.

7. The method of claim 6, further comprising selectively displaying a second virtual element on the display device, the second virtual element being configured to interact with the first virtual element.

8. The method of claim 7, wherein the second virtual element includes the virtual jaw structure.

9. The method of claim 6, wherein performing the actual manipulation and movement of the physical control element further comprises performing the actual manipulation and movement of the physical control element to impart one of translational motion and rotational motion thereto, and wherein displaying the virtual manipulation and movement of the first virtual element further comprises displaying the virtual manipulation and movement of the first virtual element as corresponding to and being the same as the one of the translational motion and the rotational motion of the physical control element.

10. The method of claim 6, wherein displaying the first virtual element on the display device further comprises displaying the first virtual element as one of a two-dimensional image and a three-dimensional image.

11. A method for planning a procedure, comprising:
displaying a first virtual element on a display device, in response to a controller device having a processor and configured to be in communication with the display device, the first virtual element comprising a virtual surgical apparatus including a virtual dental implant or a virtual surgical instrument configured to prepare a site on a virtual jaw structure to receive the virtual dental implant;

analyzing, via the processor, an actual physical manipulation and movement of a physical control element interface in communication with the controller device and configured as a corresponding scale model of the first virtual element and having six degrees of freedom of movement;

applying the analysis, via the processor, to virtually manipulate the first virtual element displayed on the display device, the virtual manipulation and movement of the first virtual element displayed on the display device corresponding to and being the same as the actual physical manipulation and movement of the physical control element interface in each degree of freedom; and directing the controller device, using a selector device operably engaged with the physical control element, to associate the physical control element with or dissociate the physical control element from the first virtual element, such that the virtual manipulation and movement of the first virtual element is the same as the actual manipulation and movement of the physical control element upon to the physical control element being associated with the first virtual element by the selector device, and such that the first virtual element is not virtually manipulated and moved upon to the physical control element being dissociated from the first virtual element.

12. The method of claim 11, further comprising selectively displaying a second virtual element on the display device, the second virtual element being configured to interact with the first virtual element.

13. The method of claim 11, further comprising selectively displaying a second virtual element including the virtual jaw structure on the display device.

14. The method of claim 11, wherein the actual manipulation and movement of the physical control element includes one of translational motion and rotational motion, and wherein the virtual manipulation and movement of the first virtual element displayed on the display device corresponds to and is the same as the one of translational motion and rotational motion imparted to the physical control element interface by the actual manipulation and movement thereof.

15. The method of claim 11, wherein displaying the first virtual element further comprises displaying the first virtual element as one of a two-dimensional image and a three-dimensional image.

16. A system comprising processing circuitry operatively coupled with a physical control element interface, wherein the processing circuitry is configured to cause the system to at least:
displaying a first virtual element on a display device, the first virtual element comprising a virtual surgical apparatus including a virtual dental implant or a virtual surgical instrument configured to prepare a site on a virtual jaw structure to receive the virtual dental implant;
analyze an actual physical manipulation and movement of the physical control element interface configured as a corresponding scale model of the first virtual element and having six degrees of freedom of movement; and
apply the analysis to virtually manipulate and move the first virtual element displayed on the display device, the virtual manipulation and movement of the first virtual element corresponding to and being the same as the actual physical manipulation and movement of the physical control element interface in each degree of freedom; and
associate the physical control element with or dissociate the physical control element from the first virtual element, in response to a selector device operably engaged with the physical control element, such that the virtual manipulation and movement of the first virtual element is the same as the actual manipulation and movement of the physical control element upon to the physical control element being associated with the first virtual element by the selector device, and such that the first virtual element is not virtually manipulated and moved upon to the physical control element being dissociated from the first virtual element.

17. The system of claim 16, wherein the processing circuitry is further configured to cause the system to selectively display a second virtual element on the display device, the second virtual element being configured to interact with the first virtual element.

18. The system of claim 16, wherein the processing circuitry is further configured to cause the system to selectively display a second virtual element including the virtual jaw structure on the display device.

19. The system of claim 16, wherein the actual manipulation and movement of the physical control element includes one of translational motion and rotational motion, and wherein the virtual manipulation and movement of the first virtual element displayed on the display device corresponds to and is the same as the one of translational motion and rotational motion imparted to the physical control element interface by the actual manipulation and movement thereof.

20. The system of claim 16, wherein the processing circuitry is further configured to cause the system to display the first virtual element as one of a two-dimensional image and a three-dimensional image.

21. A computer program product comprising at least one non-transitory computer readable storage medium having computer readable program instructions stored thereon, the computer readable program instructions comprising program instructions which, when executed by at least one processor implemented on a system for planning a procedure, cause the system to perform a method comprising:
displaying a first virtual element via a display device, the first virtual element comprising a virtual surgical apparatus including a virtual dental implant or a virtual surgical instrument configured to prepare a site on a virtual jaw structure to receive the virtual dental implant;
analyzing, via the at least one processor, an actual physical manipulation and movement of a physical control element interface configured as a corresponding scale model of the first virtual element and having six degrees of freedom of movement; and
applying the analysis, via the processor, to virtually manipulate the first virtual element displayed on the display device, the virtual manipulation and movement of the first virtual element displayed on the display device corresponding to and being the same as the actual physical manipulation and movement of the physical control element interface in each degree of freedom; and
directing the controller device, in response to a selector device operably engaged with the physical control element, to associate the physical control element with or dissociate the physical control element from the first virtual element, such that the virtual manipulation and movement of the first virtual element is the same as the actual manipulation and movement of the physical control element upon to the physical control element being associated with the first virtual element by the selector device, and such that the first virtual element is not virtually manipulated and moved upon to the physical control element being dissociated from the first virtual element.

22. The computer program product of claim 21, wherein the computer readable program instructions comprising the program instructions, when executed by the at least one processor implemented on the system, causes the system to perform the method further comprising selectively displaying a second virtual element on the display device, the second virtual element being configured to interact with the first virtual element.

23. The computer program product of claim 21, wherein the computer readable program instructions comprising the program instructions, when executed by the at least one processor implemented on the system, causes the system to perform the method further comprising selectively displaying a second virtual element including the virtual jaw structure on the display device.

24. The computer program product of claim 21, wherein the actual manipulation and movement of the physical control element includes one of translational motion and rotational motion, and wherein the virtual manipulation and movement of the first virtual element displayed on the display device corresponds to and is the same as the one of translational motion and rotational motion imparted to the physical control element interface by the actual manipulation and movement thereof.

25. The computer program product of claim 21, wherein displaying the first virtual element further comprises displaying the first virtual element as one of a two-dimensional image and a three-dimensional image.

* * * * *